United States Patent
Aberizk

(10) Patent No.: US 9,084,891 B2
(45) Date of Patent: Jul. 21, 2015

(54) PILOMOTOR EFFECT STIMULATING DEVICE AND METHOD

(76) Inventor: David Aberizk, Coronado, CA (US)

( * ) Notice: Subject to any disclaimer, the term of this patent is extended or adjusted under 35 U.S.C. 154(b) by 247 days.

(21) Appl. No.: 13/366,573

(22) Filed: Feb. 6, 2012

(65) Prior Publication Data

US 2013/0199348 A1    Aug. 8, 2013

(51) Int. Cl.
| | |
|---|---|
| *A61N 1/00* | (2006.01) |
| *A61N 1/36* | (2006.01) |
| *B26B 19/42* | (2006.01) |
| *B26B 21/40* | (2006.01) |
| *A61N 1/18* | (2006.01) |
| *A61N 1/04* | (2006.01) |
| *A61N 1/32* | (2006.01) |

(52) U.S. Cl.
CPC ............ *A61N 1/36014* (2013.01); *B26B 19/42* (2013.01); *B26B 21/405* (2013.01); *B26B 21/4081* (2013.01); *A61N 1/0452* (2013.01); *A61N 1/0476* (2013.01); *A61N 1/18* (2013.01); *A61N 1/328* (2013.01); *Y10T 83/0405* (2015.04)

(58) Field of Classification Search
CPC ............ A61N 1/00; A61N 1/02; A61N 1/04; A61N 1/18; A61N 1/40; A61B 18/18
USPC .......................... 607/145, 148, 149, 150, 151
See application file for complete search history.

(56) References Cited

U.S. PATENT DOCUMENTS

| | | | |
|---|---|---|---|
| 3,316,633 A | 5/1967 | Tapper | |
| 3,373,747 A | 3/1968 | Tapper | |
| 4,317,450 A | 3/1982 | Chalmers et al. | |
| 4,853,216 A | 8/1989 | Koslo et al. | |
| 4,980,159 A | 12/1990 | Koslo | |
| 6,083,250 A | 7/2000 | Lathrop | |
| 6,168,590 B1 * | 1/2001 | Neev | ................ 606/9 |
| 6,261,301 B1 | 7/2001 | Knesch et al. | |
| 7,584,001 B2 | 9/2009 | Beck et al. | |
| 2012/0191085 A1 * | 7/2012 | Eckhouse et al. | ............... 606/33 |

FOREIGN PATENT DOCUMENTS

| | | |
|---|---|---|
| JP | 2000-126480 | 5/2000 |
| WO | 2004073941 | 9/2004 |

OTHER PUBLICATIONS

Hellmann. "The Isolated Pilomotor Muscles as an In Vitro Preparation." J. Physiol. vol. 169. pp. 603-620 (1963).

(Continued)

*Primary Examiner* — Eric D. Bertram
*Assistant Examiner* — Elizabeth K So
(74) *Attorney, Agent, or Firm* — Procopio Cory Hargreaves & Savitch LLP

(57) ABSTRACT

A pilomotor effect stimulating device is designed to electrically stimulate the arrector pili muscles of the skin to cause a pilomotor reaction in which goosebumps are formed in the affected area and the hairs are raised away from the skin. The device has a handle and a head at one end of the handle carrying electrodes for skin application. An electronic control unit in the handle is connected to the handles and includes a pulse generator configured to produce a pulsed electrical signal at the electrodes which is designed to stimulate the arrector pili muscles in the vicinity when the electrodes are applied to the skin. The device may be used as a shaving aid to raise the hairs in an area to be shaved, making it easier to cut the hairs closer to the skin when shaving.

6 Claims, 9 Drawing Sheets

(56) References Cited

OTHER PUBLICATIONS

Hellmann. "The Effect of Temperature Changes on the Isolated Pilomotor Muscles." J. Physiol. vol. 169. pp. 621-629 (1963).

Notification, International Search Report and Written Opinion dated Feb. 28, 2013 for PCT/US2012/66950.
"The Response of the Isolated Skin of Rats to Drugs and Electrical Stimulation," by K. Hellmann, Brit. J. Pharmacol., 21, pp. 331-338, published 1963.

* cited by examiner

PILOMOTOR EFFECT STIMULATING DEVICE AND METHOD

BACKGROUND

1. Field of the Invention

The present invention generally relates to a pilomotor effect stimulating device and method for artificially producing stimulation of the arrector pili muscles of the skin to produce goosebumps and raise body hairs, and is particularly concerned with an electronic pilomotor effect stimulating device which may be used as a shaving aid.

2. Related Art

Both electronic and non-electronic shaving devices are commonly used for removing hair from various parts of the body, including facial hair for men, as well as arm, leg and underarm hair. One objective in shaving is to achieve a smooth shave removing hair down to the skin level, while not causing damage or irritation to the skin. One problem is that hair often lies relatively flat against the skin, so that the shaving device slides over some hair without cutting it. Users often try to overcome this problem by applying extra pressure to the skin, passing the shaver over the skin several times, or trying to alter the hair position relative to the blade by manually stretching the skin, facial muscle motion, or head movement. All of these actions can increase the risk of skin damage or irritation.

One technique proposed in the past for alleviating shaving irritation and inefficiency has been to apply various topical liquids or lotions to the area to be shaved, as a pre-treatment, so as to soften the hair or dry the skin so as to raise the hairs. Another shaving aid pre-treatment involves chemical stimulation of the skin to produce the so-called pilomotor effect, as described in U.S. Pat. No. 4,853,216 of Koslo et al. and U.S. Pat. No. 4,980,159 of Koslo. The pilomotor effect involves the pilomotor or arrector pili muscles of the skin which shorten when stimulated, producing "goose bumps" and causing the hair to rise to a more upright position. This effect may occur when a person is cold or experiencing emotions such as fear. It can also be produced by certain chemicals, known as alpha adrenergic receptor stimulants, when applied to the skin, as described in the cited patents. The compositions described in these patents may be applied to hair covered areas of the skin prior to shaving, causing the hair to stand up and making it easier to cut hair at a level closer to the skin.

It is also known that electrical excitation and nerve stimulation of the arrector pili muscles causes the muscles to contract and the hair to stand up for a certain time period (See The Response of the Isolated Skin of Rats to Drugs and Electrical Stimulation, by K. Hellman, *Brit. J. Pharmacol.* (1963, 21, 331-338), and this technique has been used in a laboratory setting for research purposes.

SUMMARY OF THE INVENTION

Embodiments described herein provide for a hand held electronic device designed to stimulate the pilomotor effect in human skin which may be used for various purposes, including raising or positioning the hairs for more effective shaving.

In one aspect, a hand held device for stimulating the pilomotor effect in the skin is provided which has a handle, a head having at least two spaced electrodes, and an electronic control system mounted in the handle and connected to the electrodes, the control system comprising a power supply, a controller, and a pulse generator configured to supply a pulsed electrical signal to the electrodes for application to the skin to stimulate the arrector pili muscles in the adjacent skin area.

The handle has an on-off switch for user control of the application of the pulsed signal. In one embodiment, the pulsed signal is also adjustable by the user so as to control a parameter of the signal such as the pulse width, whereby the user can increase or decrease the effect on their skin as needed. A control switch is provided on the handle for user adjustment of one or more parameters of the pulsed signal, such as the signal pulse width or intensity.

In one embodiment, the stimulating device may be designed as a shaving aid and may optionally include one or more shaving blades in the head which are spaced from the electrodes, with the electrodes located on the head in advance of the shaving blades so as to contact the skin in advance of the blades, so that the hairs are raised just before cutting, allowing cutting closer to the skin. Alternatively, the stimulating device may be applied to an area to be shaved prior to shaving, and a conventional razor or shaver may then be used to shave while the arrector pili muscles are in a stimulated condition. In other embodiments, the stimulating device may be used for other purposes such as a sexual aid, grooming, warming device, or the like.

According to another aspect, a method of stimulating the pilomotor effect in a skin area is provided which comprises running the head of a hand held pilomotor effect stimulating device over the skin area so that electrodes on the head contact the skin, and applying a pulsed electrical signal to the electrodes to stimulate the arrector pili muscles and raise hairs in the affected area. In one embodiment, the affected area is shaved while the arrector pili muscles are in a stimulated condition.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Certain embodiments as disclosed herein provide for a hand held pilomotor effect stimulating device to stimulate the arrector pili muscles and raise body hairs in an area to which the device is applied. In one embodiment, the stimulating device is used as shaving aid to position body hairs in a more erect condition for more effective shaving.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention.

Figure 1:
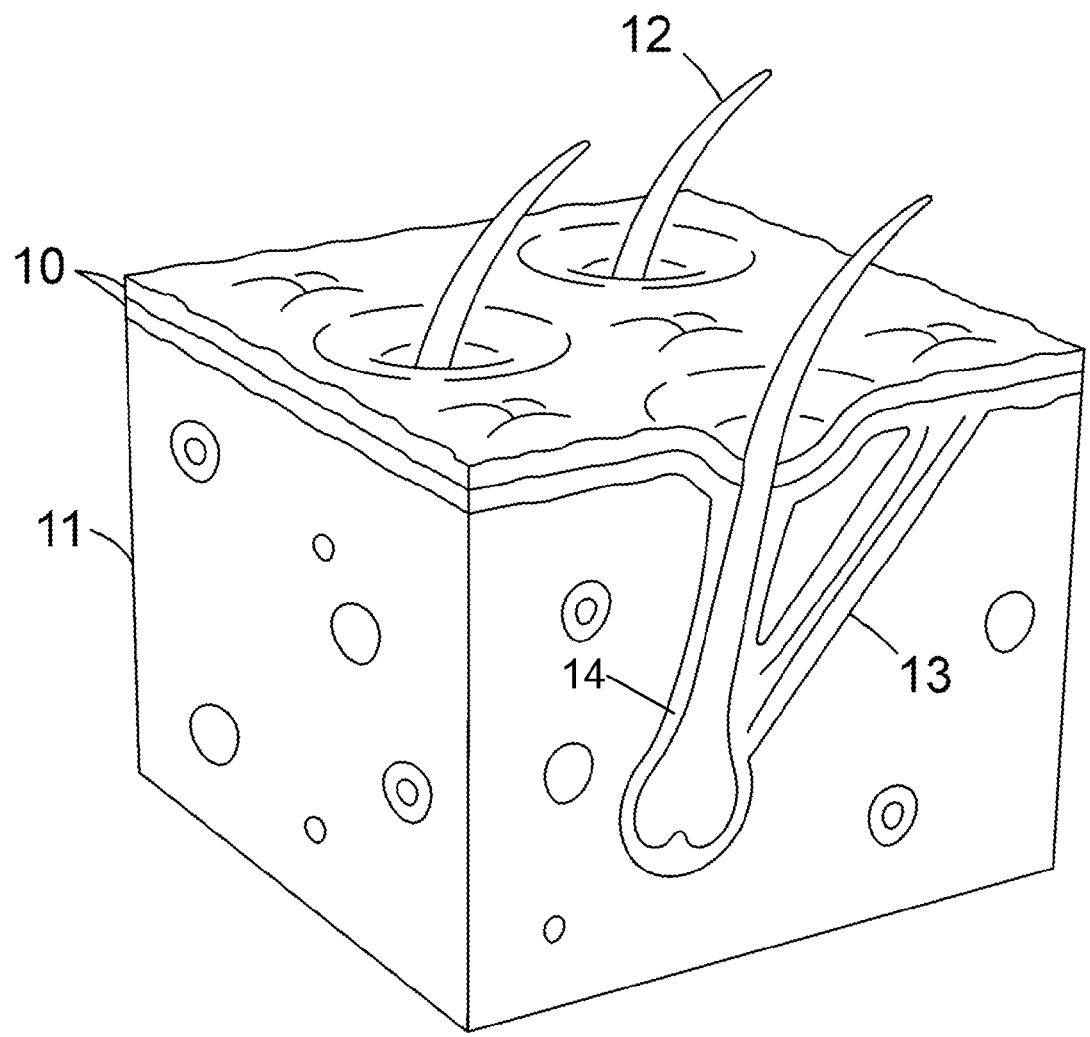
FIG. 1 is a cross section through the skin and a hair follicle, showing the arrector pili muscle in a relaxed, extended condition.
Figure 2:
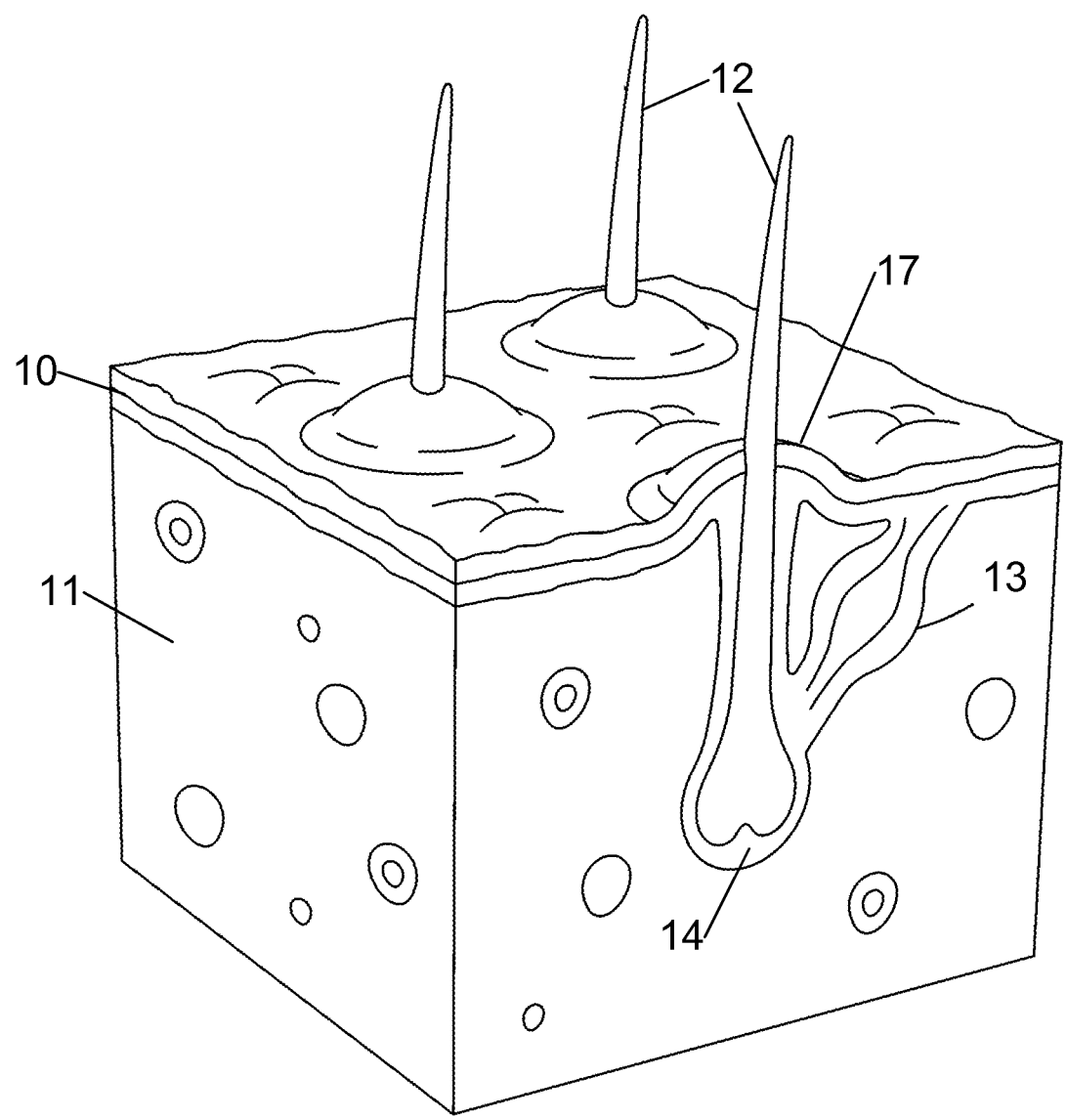
FIG. 2 is a cross section similar to FIG. 1 illustrating the arrector pili muscle in a contracted position, causing the hair to stand on end.
Figure 3:
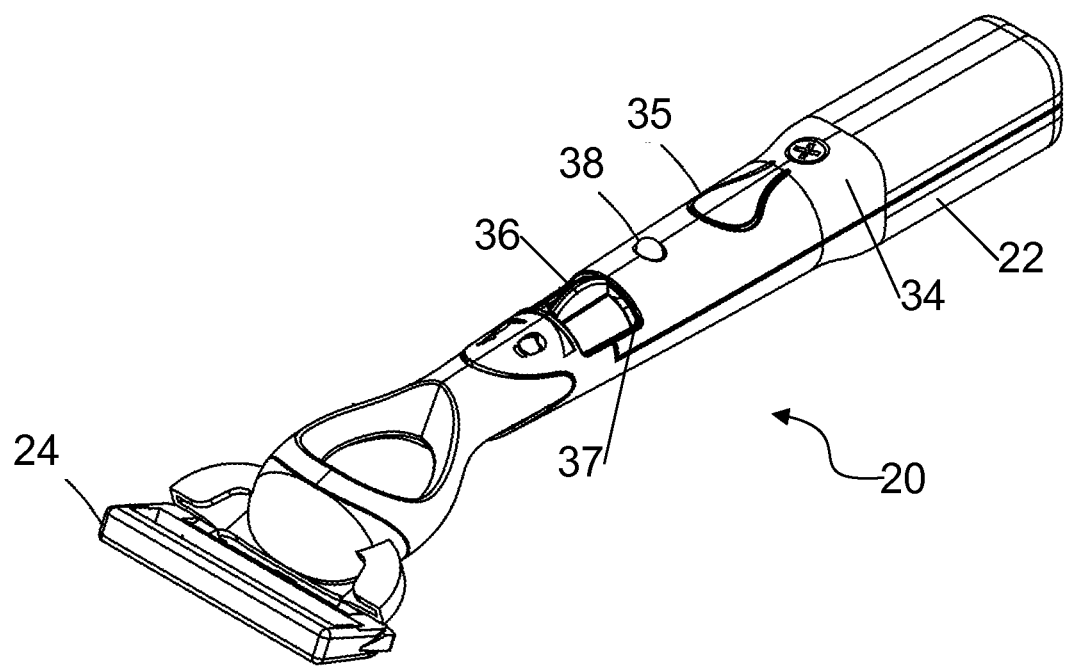
FIG. 3 is a perspective view of one embodiment of a hand held pilomotor effect stimulating device designed to stimulate the arrector pili muscles.
Figure 4:
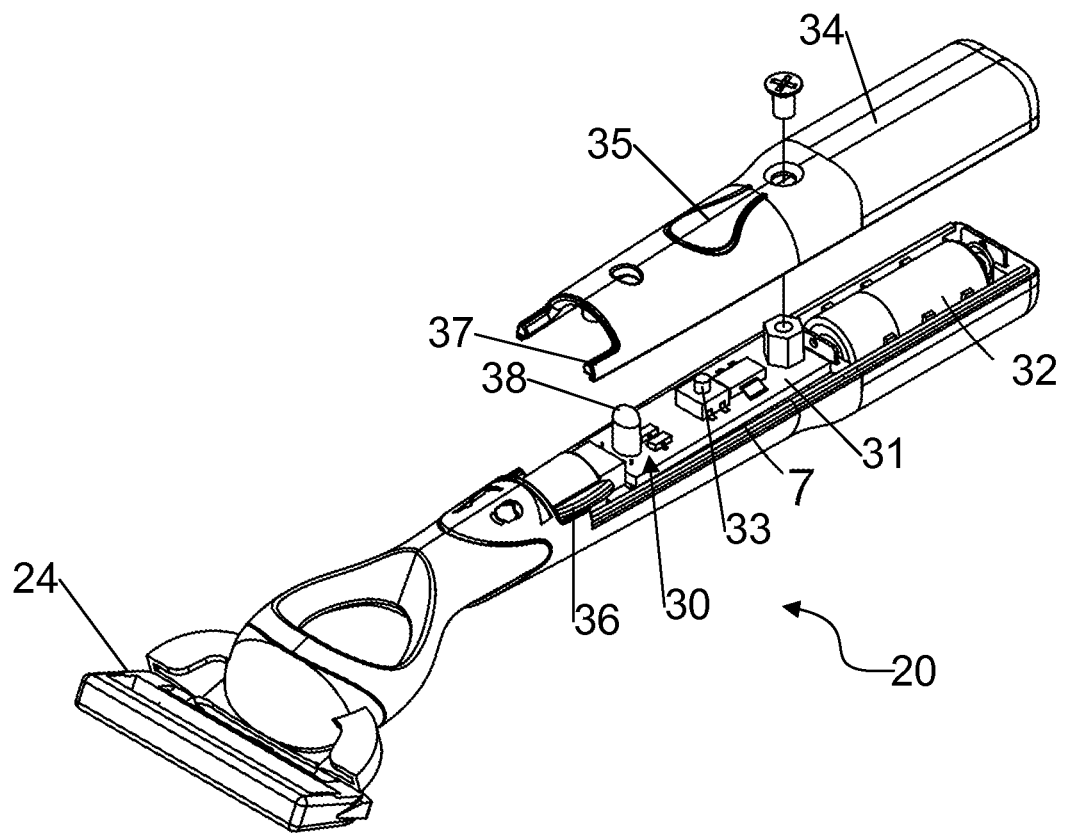
FIG. 4 is a view similar to FIG. 3 but illustrating a cover of the handle of the device removed to reveal the control circuitry and power supply of the device.
Figure 5:
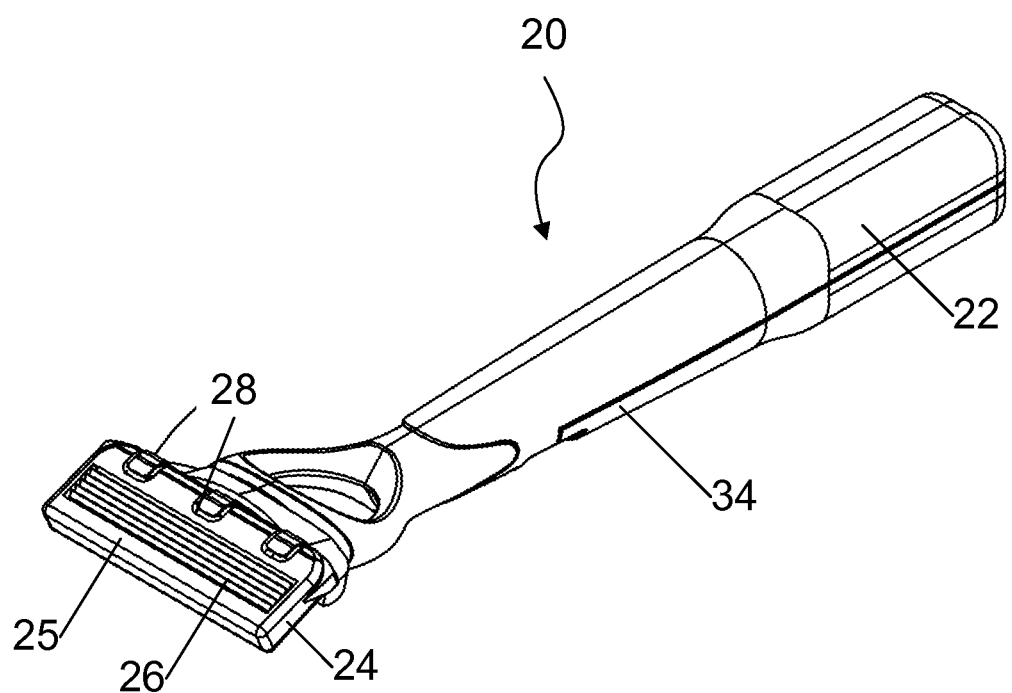
FIG. 5 is a bottom perspective view of the shaver of FIGS. 3 and 4, illustrating shaving blades in the head of the device adjacent the stimulating electrodes.

FIGS. 1 and 2 illustrate a section through the dermis 11 and epidermis 10 of the skin, illustrating a hair 12 and hair follicle 14, as well as the arrector pili muscle 13 attached to the hair follicle. FIG. 1 illustrates the muscle 13 in a relaxed, non-contracted condition, while FIG. 2 illustrates the muscle in a contracted, shortened condition such that goosebumps 17 are produced and the hair 13 stands on end or substantially straight out from the skin. This is known as the pilomotor effect, and happens naturally during stresses such as cold or fear. FIGS. 3 to 9 illustrate embodiments of a hand held pilomotor effect stimulating device 20, 50 designed to create the same effect in selected skin areas. The embodiment of FIGS. 3 to 5 is designed as a shaving aid in order to allow hair to be shaved more effectively, since hairs can be cut more readily when they stand up from the skin as in FIG. 2 rather than lay down adjacent the skin as in FIG. 1. The embodiment of FIG. 6 may also be used as a shaving aid or may be used for stimulating the pilomotor effect on the skin for other purposes.

FIGS. 3 to 5 illustrate a first embodiment of a hand held electronic device 20 designed to stimulate the pilomotor effect in human skin. As discussed above, this embodiment is designed as a shaving aid. Device 20 has a handle 22 and a head 24 having a lower face 25 configured to run over the skin. One or more shaving blades 26 are mounted in the head to project from face 25, along with two or more electrodes or probes 28 which are positioned in front of the blades to contact the skin in advance of the blades 26 as the shaving head is run over an area to be shaved. Three electrodes are illustrated in FIG. 5, but two or more than three electrodes may be used in other embodiments, with at least one positive and one negative electrode, or multiple positive or negative electrodes.

Handle 22 provides an enclosure for electronic control unit 30 and power supply or batteries 32, as illustrated in FIG. 4 where a removable cover 34 of the handle is removed to reveal the control unit. The modules and components of control unit 30 are mounted on a circuit board 31, as indicated in FIG. 4, and the output of control unit 30 is connected to the electrodes via suitable conductive wires extending from the output through the handle to the electrodes. An on-off switch 33 for the shaving aid device is actuated by push button 35 provided in cover 34 for operation by a user, and an adjustable control switch 36 for varying the pulsed electrical signal output at the electrodes or probes 28 projects outwardly from cover 34. In the illustrated embodiment, the on-off switch 33 has a push on/push off actuation, and is designed to allow the device to shut itself down after a predetermined period of inactivity. The adjustable control switch 36 comprises a sliding button or tab which the user can slide back and forth across opening 37 to control a parameter of the pulsed output signal applied at the electrodes. Other types of variable controls such as a rotating dial or the like may be used in place of slider 36. An indicator LED light 38 is also provided on the outside of the housing adjacent the switches, and is designed to indicate when the device is powered on, as well as providing a low battery indicator.

Figure 6:
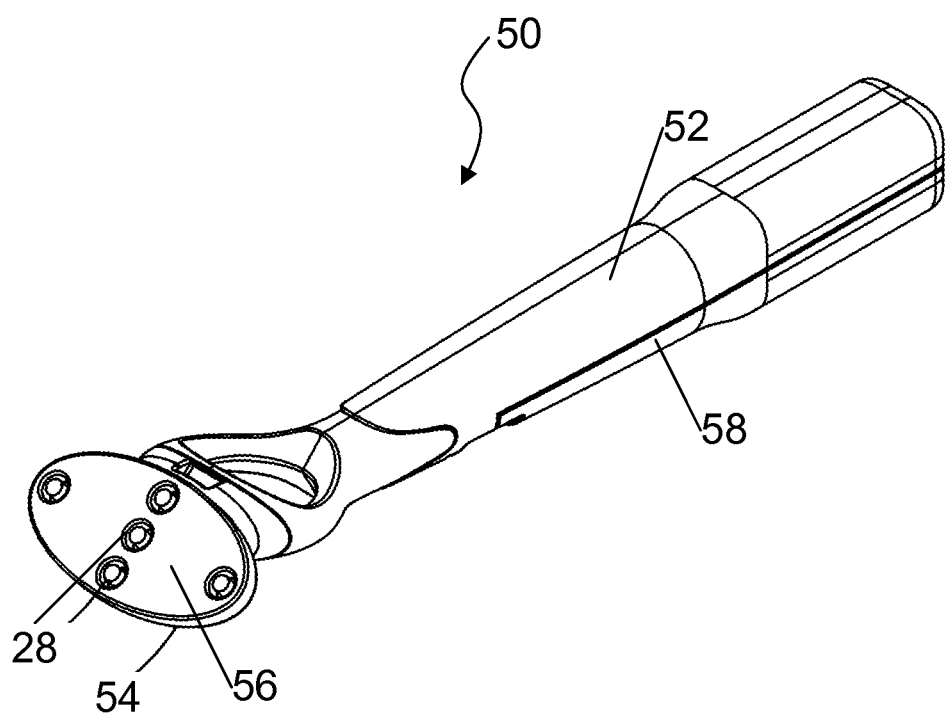
FIG. 6 is a bottom perspective view of a second embodiment of a hand held pilomotor effect stimulating device.

FIG. 6 illustrates a pilomotor effect stimulating device 50 according to a second embodiment which is similar to that of FIGS. 3 to 5 and has the same electronic control unit 30 and power supply as the previous embodiment, but which has no shaving blade or blades and may be used either as a shaving aid or for other purposes. As in the previous embodiment, device 50 has a handle 52 and a head 54 which carries a plurality of probes or electrodes 28 on its lower surface 56, but no blades. The electronic control unit 30 is enclosed in handle 52 and connected to electrodes 28. The power supply and the control unit are accessible via removable cover 34, as in the embodiment of FIGS. 3 to 5. Although not visible in FIG. 6, the device 50 has the same on-off button 35 and adjustable power control switch 38 as illustrated in FIGS. 3 and 4 for the previous embodiment, and the handle 52 is substantially identical to handle 22.

Figure 7:
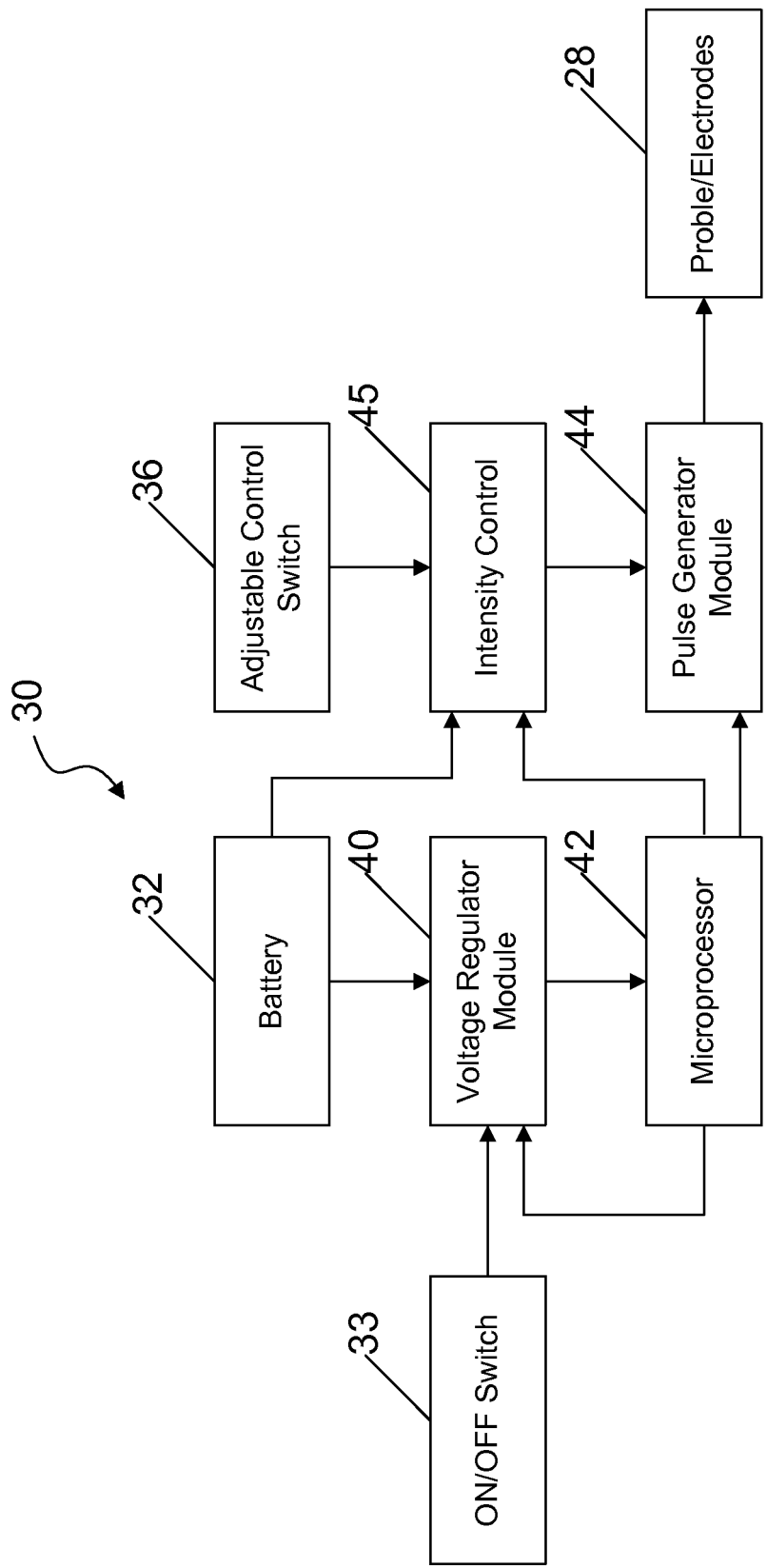
FIG. 7 is a functional block diagram of the electronic control unit of the pilomotor effect stimulating device in the embodiments of FIGS. 2 to 5 or FIG. 6.

FIG. 7 is a functional block diagram illustrating the basic components of one embodiment of the electronic control unit 30 of the shaving aid device of the embodiments described above. As illustrated in FIG. 7, control unit 30 comprises voltage regulator module 40 connected to battery 32 and on-off switch 33, a microprocessor or controller 42 connected to voltage regulator module 40, a pulse generator module 44 connected to controller 42 and having a pulsed signal output connected to electrodes 28 via electrical leads extending from the handle to the head of device 20, and an intensity control module 45 connected between battery 32 and pulse generator module 44 and controlled by adjustable control switch or slide switch 36. The controller 42 is programmed to control the pulse generator module based on inputs from the voltage regulator module and intensity or power control module 45, as described in more detail below in connection with FIG. 8.

Figure 8:
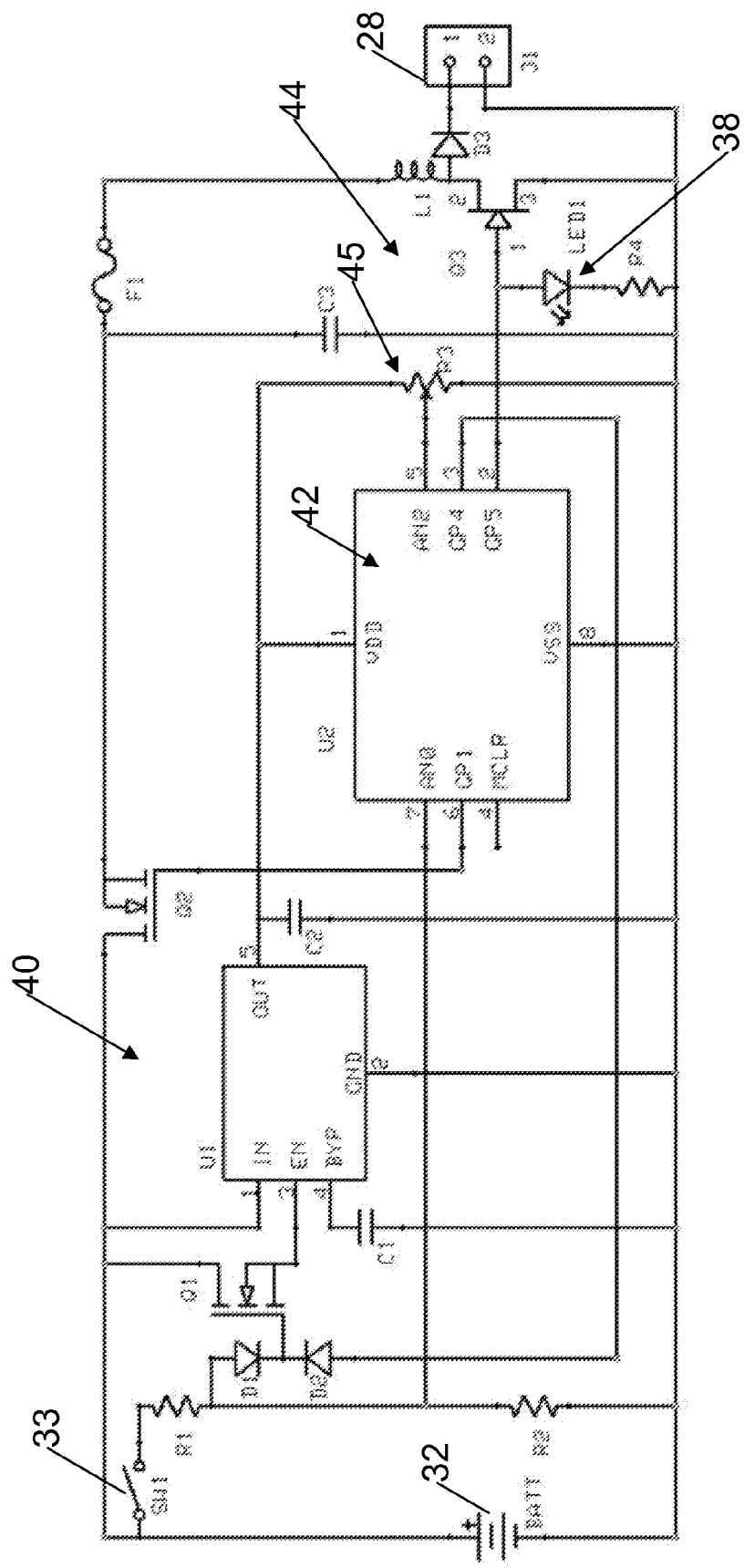
FIG. 8 is a detailed electrical schematic of the control circuitry of FIG. 7.
Figure 9:
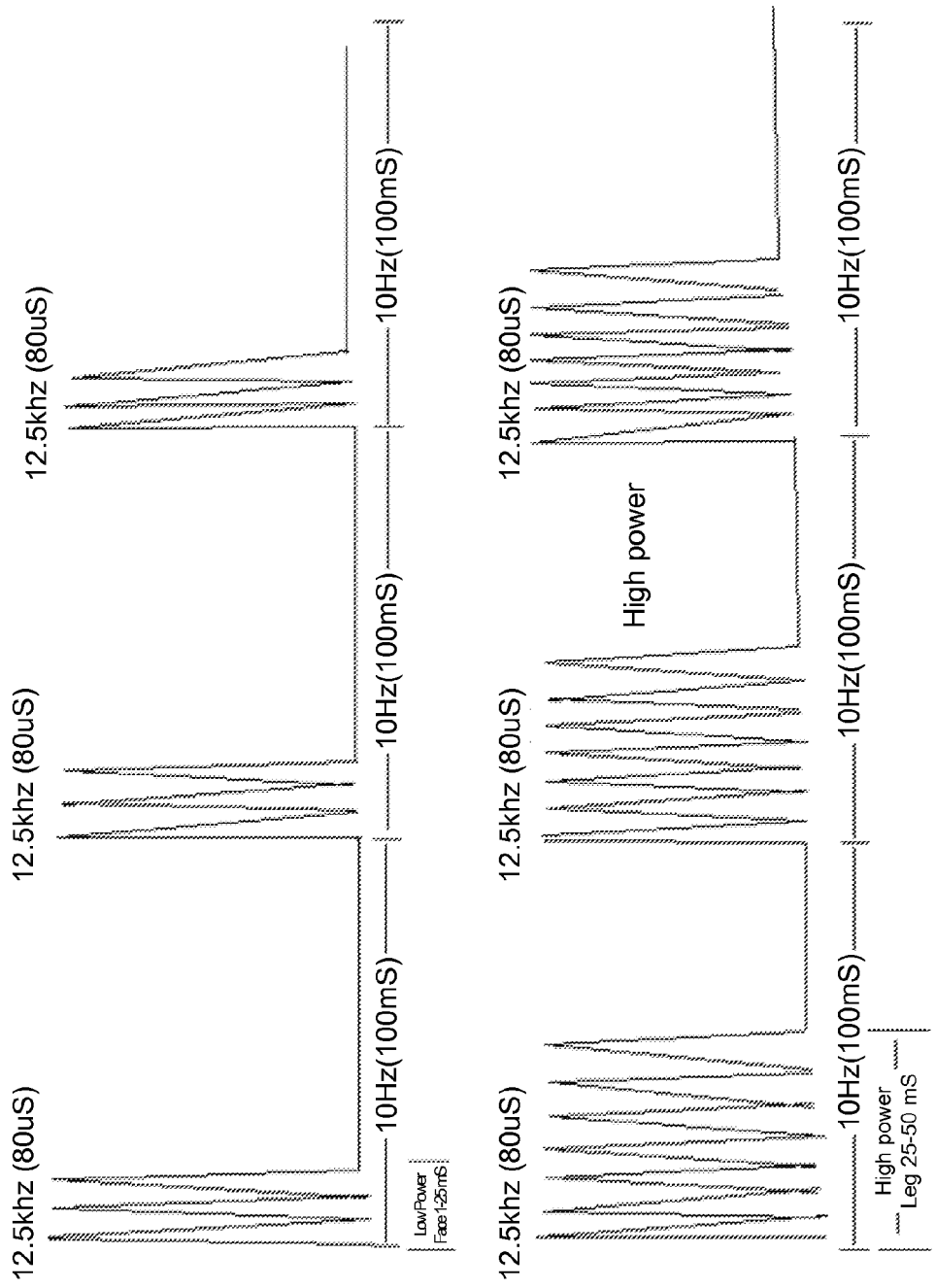
FIG. 9 illustrates examples of one embodiment of the pulsed electrical signal applied to the skin by the devices of FIGS. 3 to 8.

FIG. 8 is a more detailed schematic view of control unit 30, while FIG. 9 illustrates one embodiment of an adjustable pulsed signal produced by control unit 30 for application to the skin in order to stimulate the pilomotor effect. Pressing switch 33 (SW1) connects the voltage of battery 32 across voltage divider R1, R2. The battery may be a 12 VDC battery in one embodiment, with the midpoint of voltage divider R1, R2 referenced at 5 VDC when full and proportional to the battery charge. This reference voltage passes through D1 to the gate of Q1 which applies the full battery voltage to the enable pin 3 of the voltage regulator (U1). Upon energizing voltage regulator U1, a regulated 5 VDC is created which energizes microprocessor or control module 42 (U2). Next microprocessor U2 initializes and sets the output pin 3 at GP4 high and this signal passes through diode D2 to the gate of MOSFET Q1 to latch the power on. U2 immediately samples the reference voltage created by R1 and R2 through input pin 7 (AN0) to measure and record the battery health. If the battery is approaching the minimum operational level then light emitting diode 38 (LED1) flashes 3 times. If the battery health is satisfactory then LED1 lights up for 2 seconds.

The next step is to read the variable register R3 which is controlled by user input at adjustable control or slide switch 36. In one embodiment, movement of slide switch 36 controls pulse width of the output signal, as described in more detail below in connection with FIG. 9. In alternative embodiments, this input can control both pulse width and amplitude of the pulsed output signal from pulse generator 44. The pulse generator 44 consists of inductor L1, and FETS Q2 and Q3, capacitor C3 and diode D3. A pulse is generated by the controller U2 (42) setting the GP1 output at pin 6 high, which energizes Q2 and allows voltage to flow and charge C3. This time constant sets the intensity level. The time constant is set from the battery voltage reading on startup, and is adjusted as the battery ages to maintain a consistent output voltage. Next GP1 goes low and GP5 goes high to energize Q3 which allows the charge in C3 to flow through L1. Q3 is then turned off and L1 releases its stored energy which flows through D3 and across the output probes or electrodes 1, 2, with 1 being the positive electrode and 2 being the negative electrode. Although two electrodes are illustrated in FIG. 8, it will be understood that one, two or more positive or negative electrodes may be provided in alternative embodiments, with the embodiment of FIGS. 3 to 5 having three, with two negative and one positive or two positive and one negative, and the embodiment of FIG. 7 having five, of which the central three are positive and the outer two are negative, or vice versa.

The foregoing process is repeated at a base frequency F1, with the base signal turned on and off at a pulse repetition frequency F2, where F1 is higher than F2. Each ON pulse comprises multiple pulses at a carrier or base frequency F1, while the control of ON pulse duration determines the number of base carrier pulses applied in each ON pulse, and thus the signal intensity or power applied to the skin between the electrodes. In one embodiment, the voltage or amplitude of the pulsed signal is in the range of around 35 to 75 volts, but may be higher or lower than this in alternative embodiments, while the current is in the microamp range. The base frequency F1 may be between 10 KHz and 15 KHz. In one embodiment, the base frequency was 12.5 KHz (80 microsecond pulse width) and the pulse repetition frequency F2 was 10 Hz, as illustrated in FIG. 9, with the ON pulse width setting varying from 1 to 50 milliseconds as controlled by slide switch 36. Examples of this pulse are provided in FIG. 9, with the upper pulsed signal having a short pulse width of around 1 to 25 milliseconds, which is sufficient to stimulate the pilomotor effect in hair covered facial skin, and the lower pulsed signal having a longer pulse width of around 25 to 50 milliseconds, providing more power to stimulate the pilomotor effect in areas of higher skin resistance, such as the legs. The spacing between the positive and negative electrodes 28 in the embodiments of FIGS. 3 to 5 and FIG. 6 is no more than 0.75 inches, and is between ⅛ inch and ¾ inch for effective stimulation of the skin across which the pulsed signal is applied.

Indication of operation is provided by LED1 which flashes in response to the pulse generation signal. To de-energize the circuit, switch 33 or SW1 is pressed again and this is sensed by input AN0 of microprocessor 42 which sets GP4 low. Upon releasing the button 33, the enable is no longer held on U1 and the circuit shuts down. This also shuts off MOSFET Q2, which inhibits output of battery voltage through the probe in the off position. Since U2 has control of the enable condition, it has the ability to shutdown automatically after a predetermined period to preserve battery life, for example after around five to ten minutes. In the advent of prolonged contact between the probes or electrodes and any highly conductive material other than skin, the circuit is protected by a resettable poly fuse F1 which returns the circuit to normal operation after contact is removed.

In order to use the hand held device of FIGS. 3 to 5 to stimulate the pilomotor effect in a desired skin area, the user first turns the device on by pressing button 35, and then applies head 24 to a skin region to be shaved while gripping the handle 22, running the head over the skin and hair so as to apply the pulsed signal to the skin and raise the hairs via the pilomotor effect prior to engagement by blades 26. When using the hand held device 50 of FIG. 6, the user turns on the device and runs the electrodes on head 54 over the skin in the same way so as to stimulate the pilomotor effect, either for shaving or other purposes. In either case, the intensity of the applied pulses can be increased or decreased as desired by the user by sliding the adjustable slide switch 36 in opposite directions to increase or decrease pulse length and thus increase or decrease the pulsating charge localized between the electrodes 28. Typically, a higher charge/longer pulse width is required for leg areas with a higher skin resistance and a lower charge/pulse width for the face with a lower skin resistance. Since the effect lasts for several minutes, the user can run a razor or shaver over the skin after using device 50 to raise the hairs, with the hairs still raised or standing up from the skin area for easier cutting. The hair angle change after use of the pilomotor effect stimulating device may be detected by the user visually or by touch. The device may be used as a shaving aid for humans and for animals such as dogs to assist in grooming.

The above embodiments provide a small, lightweight and portable electronic device for stimulating the pilomotor effect in the skin for various purposes, including shaving. The first embodiment is specifically designed for shaving and incorporates one or more shaving blades after the stimulating electrodes in the head of the device. The second embodiment does not include blades and can be used to stimulate the pilomotor effect either for assisting shaving or for other purposes. When either device is used for shaving, the induced pilomotor effect in the skin area to be shaved facilitates a closer shave, without requiring application of any chemicals to the skin. The pulse width is adjustable for user preference and for different skin resistance in different individuals and for varying skin resistance in the face, arm, leg or other areas. The device is suitable for individual use since the length of the pulse is relatively short, and the output is automatically shut down in the event of a short circuit. Automatic shutdown also occurs after a predetermined time period to preserve battery life. An indicator light is provided both to indicate power on and for low battery detection, and the user can readily replace the batteries as needed.

The hand held electronic devices described above electronically induce the skin to stimulate the arrector pili muscle causing a pilomotor retraction of the hair on hair-bearing skin, as illustrated in FIG. 2, mimicking the effect of the autonomic nervous system reaction on nerve fibers that innervate them. When used as a shaving aid, this facilitates the mechanical removal of hair by using a razor or any bladed implement to slice hair down to the level of the skin, producing a closer and smoother shave, and potentially reducing irritation. This avoids any need for application of chemicals to the skin to produce more effective shaving. The small, hand held, battery operated, electrical device functions by introducing a mild pulsating charge localized between two electrode terminals at a predetermined voltage, current and frequency. The stimulating effect is localized to the general region of skin contact and is tuned to the individual pilomotor reaction by adjusting a simple slide switch on the handle of the device.

The pulsed electrical signal used to stimulate the pilomotor effect in the devices described above comprises a series of high frequency pulses which alternate ON and OFF at a lower frequency repetition rate. The voltage minimum to produce the effect is around 30 volts peak to peak, with a high frequency or base frequency for the signal of around 10 to 15 KHz and an adjustable ON pulse length of between 1 and 50 ms and a pulse repetition rate of 10 Hz. It has been found that user variation of the ON pulse length provides better control of the applied power level to adjust for individual skin zone resistance and user preference.

The control circuit in the illustrated embodiment uses a small inductor L1 in an inductor fly back design rather than a transformer, for power conservation. The disadvantage of this design is that it allows a DC bias to flow to the output electrodes when not oscillating. This drawback is overcome by providing short circuit protection via fuse F1 or by a controlled switch, or both.

Those of skill will appreciate that the various illustrative logical blocks, modules, circuits, and algorithm steps described in connection with the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block or step is for ease of description. Specific functions or steps can be moved from one module or block without departing from the invention.

The various illustrative logical blocks and modules described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium. An exemplary storage medium can be coupled to the processor such that the processor can read information from, and write information to, the storage medium. In the alternative, the storage medium can be integral to the processor. The processor and the storage medium can reside in an ASIC.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. A pilomotor effect stimulating device, comprising:
a handle having opposite first and second ends and configured for gripping by a user;
a head secured to the second end of the handle and having at least two spaced electrodes configured for application of a pulsed electrical signal to an area of skin covered by hair;
a power supply mounted in the handle;
an electronic control unit mounted in the handle and connected to the power supply and the electrodes;
a user operable switch in the handle configured to control connection of the power supply to the electronic control unit;
the control unit comprising a control module and a pulse generator configured to communicate a pulsed electrical signal to the electrodes for application to the skin to stimulate arrector pili muscles of hairs in a stimulated area in the vicinity of the electrodes and raise the hairs in the stimulated area;
the pulsed electrical signal comprising two superimposed pulse frequencies at frequencies F1 and F2, where frequency F1 is a predetermined base carrier frequency F1 and frequency F2 is a predetermined frequency lower than frequency F1, wherein the control module is configured to turn the pulse generator on and off to produce ON pulse periods separated by OFF periods of no pulses at a pulse repetition rate of the second frequency F2, where each ON pulse period comprises multiple pulses of base carrier frequency F1 and the base frequency F1 is in the range from 10 KHz to 15 KHz; and
a manual, user operable adjuster switch configured to vary the ON pulse period, whereby the user controls the number of pulses at base frequency F1 in each ON pulse period.

2. The device of claim 1, wherein the width of the ON pulse period is variable in a range from 1 to 50 milliseconds.

3. The device of claim 1, wherein the frequency F2 at which the ON pulse period repeats is 10 Hertz independent of the width of the ON pulse period.

4. The device of claim 1, wherein the pulses in each ON pulse period have an amplitude in the range from around 30 to 75 volts.

5. The device of claim 1, further comprising at least one shaving blade located on the head and spaced from the electrodes.

6. The device of claim 1, wherein the base frequency F1 is 12.4 KHz.

* * * * *